United States Patent [19]

Alt

[11] Patent Number: 5,003,976

[45] Date of Patent: Apr. 2, 1991

[54] CARDIAC AND PULMONARY PHYSIOLOGICAL ANALYSIS VIA INTRACARDIAC MEASUREMENTS WITH A SINGLE SENSOR

[76] Inventor: Eckhard Alt, Eichendorffstrasse 52, 8012 Ottobrunn, Fed. Rep. of Germany

[21] Appl. No.: 250,155

[22] Filed: Sep. 28, 1988

[30] Foreign Application Priority Data

Sep. 28, 1987 [DE] Fed. Rep. of Germany ....... 3732640

[51] Int. Cl.⁵ ............................................ A61N 1/368
[52] U.S. Cl. ........................... 128/419 PG; 128/419 P; 128/671; 128/672
[58] Field of Search ................ 128/671, 672, 670, 723, 128/734, 419 P, 419 PG

[56] References Cited

U.S. PATENT DOCUMENTS

| | | | |
|---|---|---|---|
| 3,587,562 | 6/1971 | Williams | 128/696 |
| 3,593,718 | 7/1971 | Krasner et al. | |
| 3,608,542 | 9/1971 | Pacela | 128/723 |
| 4,291,699 | 9/1981 | Geddes et al. | |
| 4,399,820 | 8/1983 | Wirtzfeld et al. | |
| 4,535,774 | 8/1985 | Olson | |
| 4,566,456 | 1/1986 | Koning et al. | |
| 4,567,892 | 2/1986 | Plicchi et al. | |
| 4,576,183 | 3/1986 | Plicchi et al. | |
| 4,596,251 | 6/1986 | Plicchi et al. | |
| 4,671,296 | 6/1987 | Aitken | 128/671 |
| 4,674,518 | 6/1987 | Salo | |
| 4,686,987 | 8/1987 | Salo et al. | 128/419 PG |
| 4,688,573 | 8/1987 | Alt | |
| 4,694,830 | 9/1987 | Lekholm | |
| 4,697,591 | 10/1987 | Lekholm et al. | |
| 4,702,253 | 10/1987 | Nappholz et al. | |
| 4,719,921 | 1/1988 | Chirife | 128/419 PG |
| 4,721,110 | 1/1988 | Lampadius | |
| 4,722,342 | 2/1988 | Amundson | |
| 4,730,618 | 3/1988 | Lekholm et al. | 128/419 PG |
| 4,757,815 | 7/1988 | Strandberg et al. | 128/419 PG |
| 4,790,318 | 12/1988 | Elmqvist et al. | 128/723 |
| 4,805,621 | 2/1989 | Heinze et al. | 128/734 |
| 4,805,629 | 2/1989 | Farges | 128/671 |
| 4,823,797 | 4/1989 | Heinze et al. | 128/671 |
| 4,901,725 | 2/1990 | Nappholz et al. | 128/419 PG |

FOREIGN PATENT DOCUMENTS

| | | |
|---|---|---|
| 0059868 | 2/1982 | Fed. Rep. of Germany . |
| 3428975 | 8/1984 | Fed. Rep. of Germany . |
| 8505279 | 12/1985 | Fed. Rep. of Germany . |
| 8713037 | 9/1987 | Fed. Rep. of Germany . |

OTHER PUBLICATIONS

"Pulmonary Blood Flow and Venous Return During Spontaneous Respiration", G. A. Brecher et al., *Circulation Research*, vol. III, Mar. '55, pp. 210–214.
"Subselective Measurement of Coronary Blood Flow Velocity Using a Steerable Doppler Catheter", D. H. Sibley et al., *JACC*, vol. 8, No. 6, Dec. '86, 1332–1340.

*Primary Examiner*—Lee S. Cohen
*Assistant Examiner*—Kennedy J. Schaetzle
*Attorney, Agent, or Firm*—Laurence R. Brown

[57] ABSTRACT

Physiological activity of a patient is detected and analyzed by means of a single sensor situated in the vascular system of the patient. Pulmonary activity is derived from analysis of changes in cardiac activity, such as sensed from blood flow, pressure or volume changes, measured in a preferred embodiment as impedance change within the right heart. Pulmonary activity is separated from cardiac activity implicit in such changes by filtering lower and higher frequency components. The separated signals are processed to derive control signals for stimulating the heartbeat in a pacemaker system, preferably by a single sensor-stimulator electrode implanted within the right heart. Thus, a single functional parameter, namely intra-cardiac impedance, varying both with the intrathoracic pressure fluctuations following respiration and with cardiac contraction is representative of the pulmonary activity and of the cardiac activity. Resulting derived sub-signals then provide information regarding cardiac and pulmonary activity and are used to monitor the patient's condition and control variably the rate of a cardiac pacemaker.

27 Claims, 7 Drawing Sheets

CARDIAC AND PULMONARY PHYSIOLOGICAL ANALYSIS VIA INTRACARDIAC MEASUREMENTS WITH A SINGLE SENSOR

TECHNICAL FIELD

This invention relates to the analysis of instantaneous physiological parameters affecting the heart and lungs and more particularly it relates to means and methods of measuring with a single sensor both cardiac and pulmonary physiological parameters of a patient to derive and analyze data useful in treating the patient for cardiac and pulmonary conditions such as the control of a cardiac pacemaker in accordance with dynamic changes incurred in physiological activity of the patient.

BACKGROUND ART

In modern intensive medicine a successful therapeutic intervention is only possible on the basis of extensive diagnostic information. Knowledge of cardiac and respiratory activity as physiological functional parameters is essential. They are usually monitored using a plurality of measuring elements such as cardiac catheters, special breathing sensors, etc. For this monitoring, not only is the display and evaluation of the functional parameters difficult to coordinate, but also the placement of the detection instruments within the heart and lungs of a patient is difficult.

Many such functional parameters are also dependent upon a patient's exercise, so that they can also be used to control dynamic variations in the pacing rate of a cardiac pacemaker.

Some available publications describe pacing rate control of a pacemaker by measured signals based on the detection of one physiological functional parameter. Thus, in U.S. Pat. No. 4,566,456, G. Koning et al., Jan. 28, 1986, the systolic pressure and change in time of the right ventricular pressure is used as the functional parameter. In German Offenlegungsschrift No. 27 17 659, A Wirtzfeld, et al., published Oct. 26, 1978, the central venous oxygen saturation parameter is used. In U.S. Pat. No. 4,535,774, W. H. Olson, Aug. 20, 1985 and U.S. Pat. No. 4,674,518, R. W. Salo, June 23, 1987, the ventricular stroke volume of the heart is determined by means of an impedance measurement. In U.S. Pat. No. 4,567,892, G. Plicchi, et al., Feb. 4, 1986, the respiratory rate is determined from an implanted secondary electrode by an impedance measurement. In U.S. Pat. No. 4,697,591, A. Lekholm, et al., Oct. 6, 1987, the respiratory rate is determined from impedance across the chest cavity by using the can and heart implant electrodes. In U.S. Pat. No. 4,596,251, G. Plicchi, et al., June 24, 1986, the respiratory minute volume is measured by impedance changes from at least one electrode located in the chest cavity. Other related respiratory rate controls are effected in U.S. Pat. Nos.: 3,593,718, J. L. Krasner et al., July 20, 1971; 4,721,110, M. S. Lampadius, Jan. 26, 1988 and 4,702,253, T. A. Nappholz et al., Oct. 27, 1987. In U.S. Pat. No. 4,291,699, L. A. Geddes, et al. Sept. 29, 1981 the change of impedance between two electrodes in one ventricle is used to indicate and control fibrillation of the heart. In U.S. Pat. No. 4,576,183 G. Plicchi, et al., Mar. 18, 1986 subcutaneous electrodes in a patient's chest are used to measure impedance for obtaining a respiratory parameter.

Recently there have also been proposals to control the pacing rate of a cardiac pacemaker from two or more physiological functional parameters. In German Patent No. P 36 31 155.C2, published Mar. 24, 1988, pacing rate is controlled for stable long-term control from the temperature of the venous blood within the heart and from an activity sensor for short-term exercise related activity. The temperature signals can be modulated by the activity signals for an optimal adaptation of the pacing rate to the particular exercise of the patient. Different sensors may be used to check the two functional parameters. The pacemaker control is based on the finding that essentially only absolute parameters such as the blood temperature and activity should be used as absolute values for determining a relationship between these parameters and the pacing rate, whereas other physiological functional parameters are merely relative parameters, which at least impede stable long-term control of the pacemaker.

U.S. Pat. No. 4,722,342, D. Amundson, Feb. 2, 1988 provides a plurality of different body activity sensors to derive variable pacer controls for body activity.

SUMMARY OF THE INVENTION

In this and related prior art instrumentation for analyzing a patient's physiological condition as related to desired and actual cardiac activity there are unresolved problems corrected by this invention. Thus, the prior art does not provide simple easy to install in the patient detectors, nor do the detectors produce adequate physiological functional parameters providing little possibility of error in derived signals for introducing dynamic changes in heartbeat stimulus produced by pacemakers.

For example, when multiple sensors are used at different body locations, such as chest and heart cavities, not only is there a chance for erroneous control signals, but there is the corresponding necessity to implant special detectors for this purpose. The chances for control error may be typified by the measurement of impedance across a chest cavity to derive ventilatory response signals under different conditions of activity. Thus, the measured impedance can vary with the position of a patient's body or arm, and is not solely restricted to the period or magnitude of inspiration or expiration. Thus, false control signals could adjust the pacing rate in response to sensed respiratory physiological parameters. Such false signals can also come from interference between multiple sensors and complex processing systems for analyzing and merging various detected signals.

Another problem with prior art sensors is the ability to dynamically respond closely enough to real time to those physiological parameters of a patient that produce proper control signals for heartbeat stimulus provided by a pacemaker. Thus, for example, temperature measurements slowly respond and pressure measurements are subject to outside noise influences such as coughing or sneezing that should not affect the heartbeat rate.

The simplicity of prior art detectors was primarily due to the use of a single variable such as respiratory or blood pressure fluctuations. However, this does not give enough data for successful diagnosis, therapy or pacing rate control. Thus, the problem of simplicity in system and installation of detectors has not been resolved in such a way to produce the desired physiological parameters for analysis and control. The present invention thus affords a single sensor within the heart operable to measure a single intracardiac functional parameter, and means to derive from that measurement both pulmonary activity and cardiac activity. This detector in the case of a patient having a pacemaker is the already implanted stimulus electrode, preferably on the right side of the heart and to use that electrode both as an intracardiac detector and as a heart pacer.

Accordingly, both intracardiac pressure fluctuations correlating with the patient's breathing and physiological signals coming from the heart itself can be detected using only one measuring element located within the heart and detecting only one integral intracardiac functional parameter.

Investigations by applicant correlate breathing and intrathoracic pressure fluctuations with physiological parameters of blood measured in the heart. Thus, for example, a single sensor in the right ventricle can determine from changes of blood parameters, preferably impedance, the necessary functional parameters for proper heartbeat rate control of a pacemaker, namely the rate and depth of respiration, contractility of the myocardium, stroke volume, etc.

Great advantages are obtained in control of a cardiac pacemaker in response to these detected signals. Significant is the simple construction with the measuring element constituting the simultaneously used stimulation electrode, thus necessitating no further implants.

An essential advantage of the invention is that the sole intracardiac measurement, preferably impedance, allows for respiratory and cardiac functional parameters to be clearly distinguished from each other by appropriate filtering with respective high pass and low pass filters. This is not possible with prior art measurements such as the impedance measurement of breathing with a thoracic secondary electrode, in part because the respiratory effects on the signals detected are such that the overall information signal has little indicative value and is superimposed with high interference. Such mutual interference of respiratory or pulmonary and cardiac functional parameters is reliably eliminated by this invention.

BRIEF DESCRIPTION OF THE DRAWINGS

The invention shall be explained in more detail in an exemplary embodiment in connection with a cardiac pacemaker with reference to the accompanying drawings, in which.

THE PREFERRED EMBODIMENTS OF THE INVENTION

Figure 1:
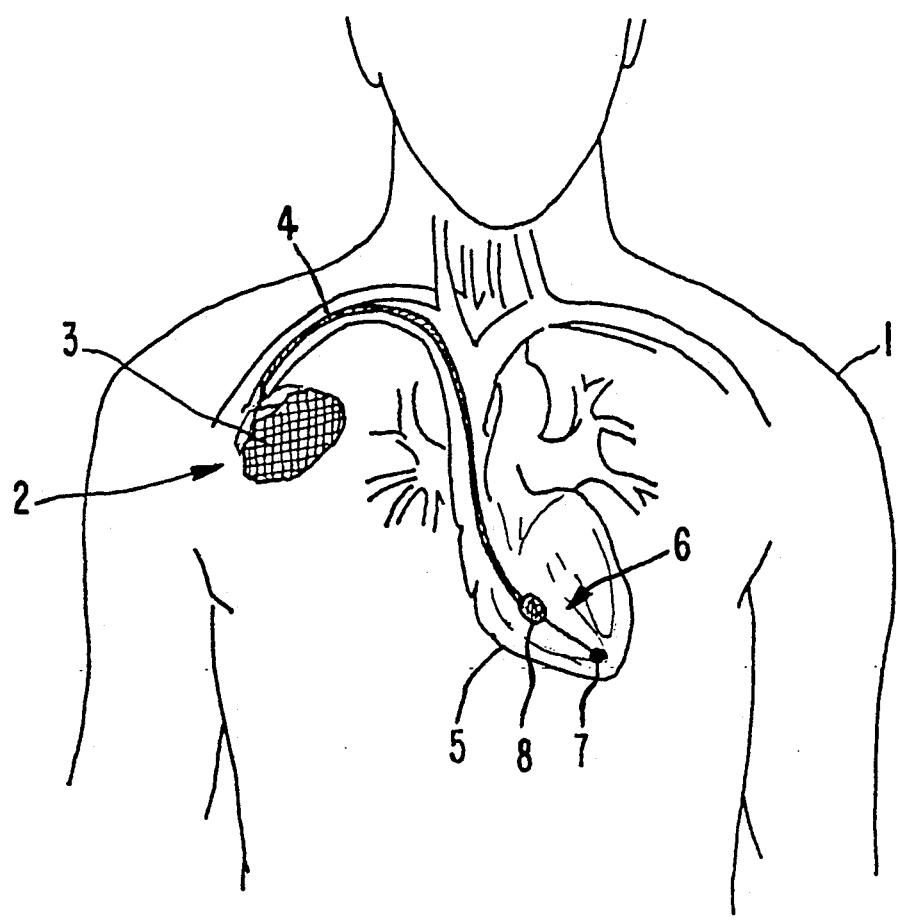
FIG. 1 shows a schematic view of an inventive cardiac pacemaker electrode system implanted in a patient's heart.
Figure 2:
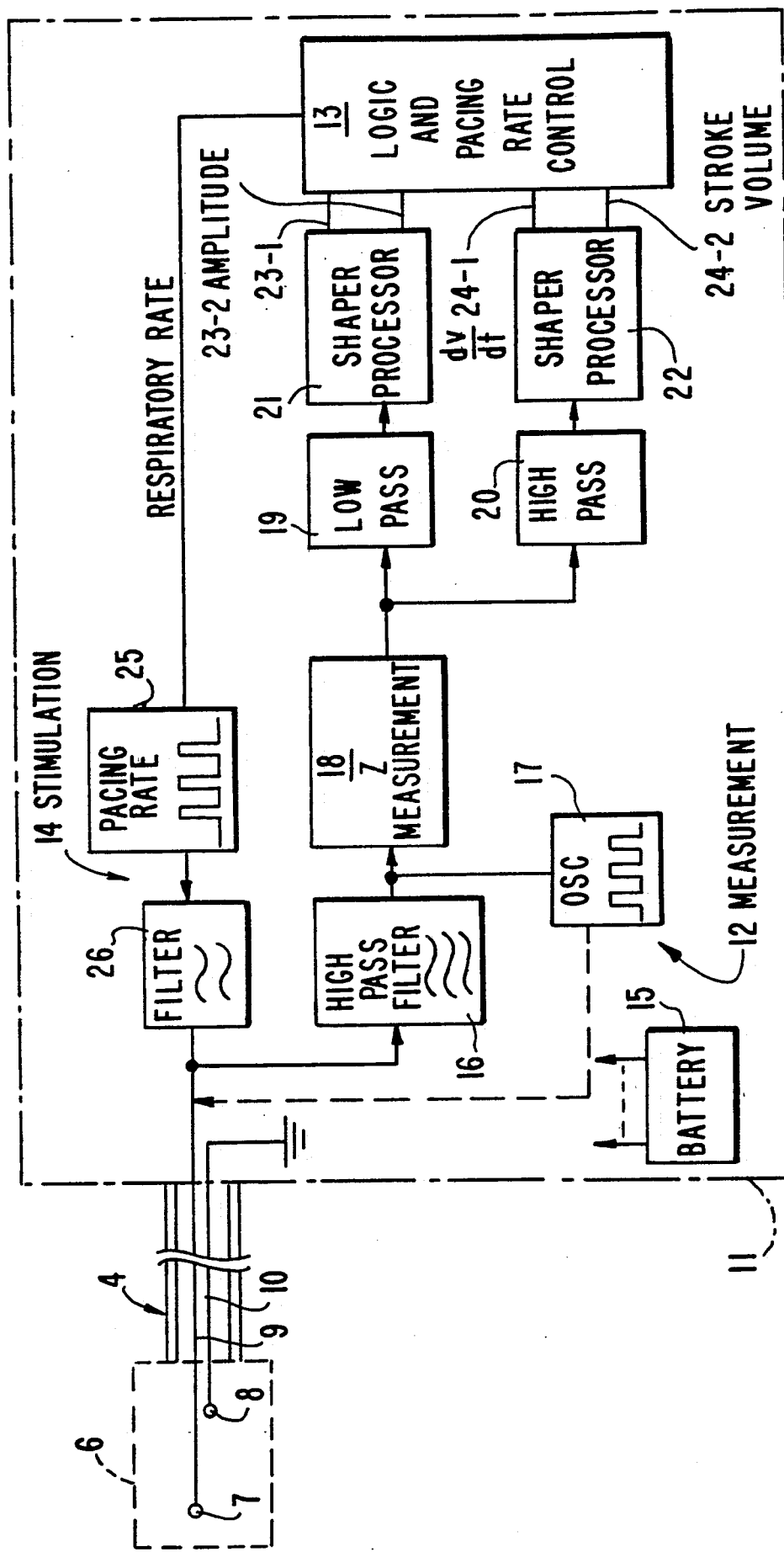
FIG. 2 shows in block diagram form the electronic diagnosis system afforded by this invention.

FIG. 1 shows a cardiac pacemaker 2 implanted in a patient 1, comprising a can 3 from which a probe 4 leads via a vein into heart 5. Probe 4 is designed at its front end located in the ventricle as a single sensor 6, which in this embodiment has a first electrode pole 7 located at the tip of the probe 4 and a second electrode pole 8 located more proximally. As seen from FIG. 2, electrical lines 9 and 10 within probe 4 connected the two spaced poles 7 and 8 located within the right ventricle with a control circuit 11 disposed in can 3.

The block diagram control circuit 11 has functionally defined control circuit elements which can be embodied into an integrated circuit along with associated microprocessing means and appropriate software. The control circuit comprises generally a measurement section 12, a logic section 13 and a stimulation section 14. Energy is supplied by battery 15.

One line 10 from detector electrode pole 8 is connected to ground potential. The other detector signal line 9 is coupled to the signal measurement section 12 by high pass filter 16. An oscillator 17 provides alternating current of low amplitude unable to pace the heart for impedance measurement with a frequency between approximately 1 kHz and 100 kHz that does not interfere with pacer stimulation. A low current amplitude in the range of a few microamperes, or alternatively single pulses of 0.01 msec duration and amplitude of less than a milliampere, reduces battery load. The current signal of oscillator 17 is also applied in addition to the stimulus pacer signal 25 to the measuring-stimulus electrode 6 by way of the dotted lead. This is an interrogating electric signal which responds at the single sensor 6 to variations of cardiac activity and of pulmonary activity to produce a single variable signal representative of heart and pulmonary activity, and has such low energy that it does not pace or stimulate the heart, nor interfere with the pacer signals 25.

Physiological activity detection or measuring means 18 then processes the single variable signal or subsignal derived from it such as the lower and higher frequency components of the dynamic signals sensed at electrode 6 and modulated on the high frequency oscillations from oscillator 17 supplied via filter 16. This single variable signal responds to the changes in physiological parameters such as changes in volume, flow or pressure in the patient's vascular system preferably within the right heart. The preferred embodiment of a detection and measurement system for this purpose responds to the variations of blood impedance indirectly indicating the changes in volume.

Accordingly the resistance (or impedance) within the heart between the single sensor 6 electrode poles 7 and 8, as defined by Ohm's law, is determined in the impedance measuring means 18 following high-pass filter 16 which transmits the carrier signals from the single signal reproduced by sensor 6 varying with cardiac and pulmonary activity modulated upon the oscillator 17 signal frequency, and rejects the pacing signals 25 passed through low-pass filter 26. The resulting raw signal varying dynamically in impedance is fed on one hand to a low-pass filter circuit 19 and on the other hand to a high-pass filter circuit 20, which splits the impedance modulated signal into lower and higher frequency subsignal portions. Thus, low-pass circuit 19 passes physiological activity signals associated with the patient's lower rate respiratory activity, whereas high-pass circuit 20 passes physiological activity signals associated with the patient's cardiac activity. Since the heart rate is generally four to five times greater than the respiratory rate, these respiratory or pulmonary and cardiac signals can be separated by filters within the known state of the art.

The output signals of low-pass and high-pass circuits 19, 20 are each fed to a respective signal shaping circuits 21, 22 for pre-evaluation, e.g. averaging, determination of the derivative in time, evaluation of amplitude and frequency and subsequent integration, or the like. An output line 23-1 of low-pass circuit 21 then provides a signal associated with the respiratory rate and corresponding to the periodic frequency of the low-frequency signal. The further output line 23-2 provides a signal associated with the depth of respiration and corresponding to the amplitude of the low-frequency signal. An output line 24-1 of high-pass circuit 22 provides a signal associated with the contractility of the heart and corresponding to the derivative in time (dV/dt) of the high-pass filtered impedance signal, i.e. the rate of change in time of the systolic stroke volume. A further output line 24-2 provides a signal associated with the stroke volume of the heart and corresponding to the amplitude of the high-passed impedance signal.

All output lines 23, 24 are connected to logic circuits 13, which calculate on the basis of available signals, an optimum pacing rate related to the exercise of the pacemaker wearer. As represented in the above mentioned prior art, it is known in the art how to use physiological signals to control the pacing rate signals 25 for a heart pacer. This pacing rate is fed to a pulse generator 25 in stimulation signal section 14, which provides corresponding stimulation pulses to the single sensor electrode 6 via a filter 26. The frequencies of measuring channel 12 and stimulation channel 14 are separated by filters 16 and 26 so that the signals in one channel do not interfere and impair the functioning of the other channel. In this manner the single sensor electrode 6 can be used both as a measuring electrode and as a stimulation electrode.

Figure 3:
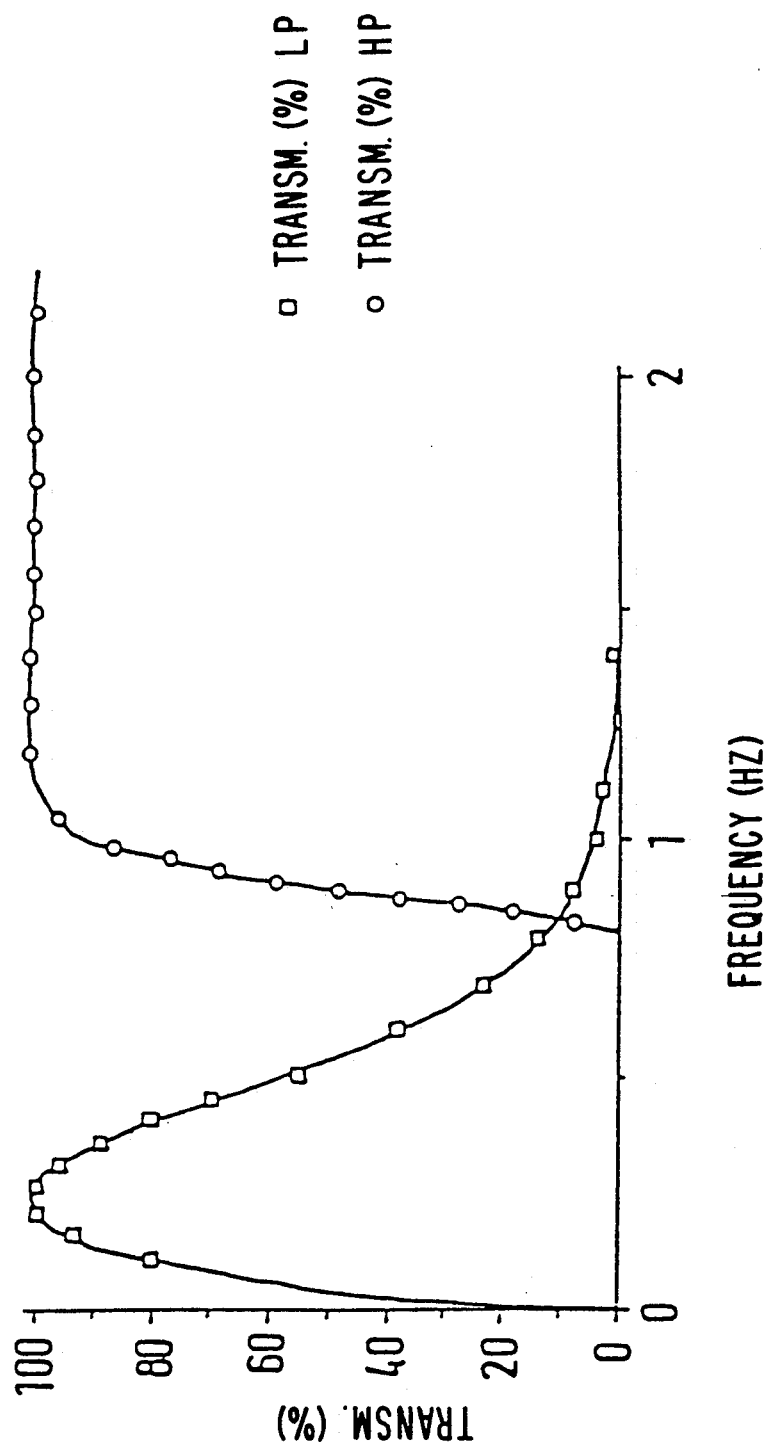
FIG. 3 is a waveform diagram showing the bandwidth characteristics of the respiratory and cardiac signal components for forming low-pass and high-pass filters.

FIG. 3 in the lower frequency curve denoted by the square coordinate markers the filter characteristic of low-pass filter 19 are typified. It is seen that the degree of transmission stated in % has dropped virtually to zero at a frequency of one hertz. Signals correlating with cardiac activity have a frequency higher than this value, so that there is no interference with the low-passed signals representative of breathing rate. The low-passed breathing signals are processed in signal shaping circuit 21, and if necessary can be amplitude corrected to allow for filter characteristics, to provide signals for evaluation of the amplitude of respiration. The filter characteristics of the high-pass circuit 20, as shown by the curve with the circular coordinate points, permits the signals based on cardiac activity to pass without interference with or distortion by the respiratory signals.

Figure 4:
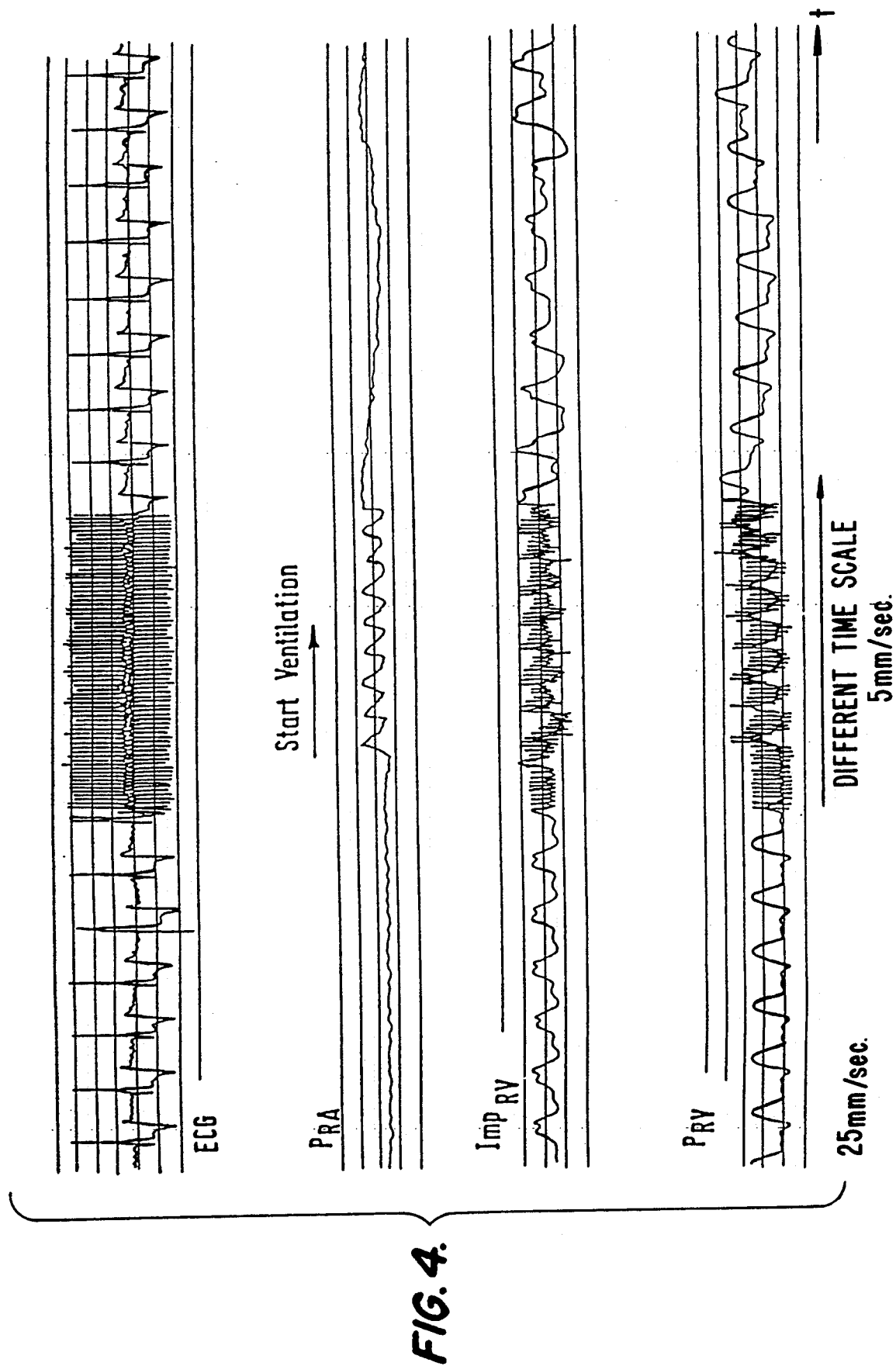
FIGS. 4, 5 and 6 are signal waveform diagrams illustrating the impedance curves for intracardiac measurements in animals, with various parameters.

As shown in FIG. 4 in numerous measurements with animals, and with corresponding tests on more than twenty healthy persons and pacemaker patients, applicant has confirmed the features on which the invention is based. An initial series of tests on dogs shows that changes in intracardiac physiological parameters, i.e., pressure, volume and the corresponding flow through the heart, correspond to cardiac activity, upon which changes due to the respiratory activity are superimposed. More on these changes in flow following respiration has been disclosed in an article by Gerhard A. Brecher, published in *Circulation Research*, Volume III, Mar. 1955, pp. 210 to 214. Appropriate alternative means to measure flow within the vascular system are known from the publication, "Subselective Measurement of Coronary Blood Flow Velocity Using a Steerable Doppler Catheter," by David H. Sibley, et al. in *JACC*, Vol. 8, No. 6, Dec. 1986, pp. 1332-1340.

In the same series of tests it was also shown that myocardial contractility exerts an influence on the rate of change in time of the pressure and volume change due to heartbeat within one heartbeat in the right ventricle. The reference waveform is the electrocardiogram ECG, with the indirect volume measurement taken by impedance measurement shown as oscillation signals occurring during the ventilation period and superimposed on the cardiac activity waveform. The pressure ($P_{RA}$) within the right atrium during a series of heartbeats is prominently shown to be influenced by intervening pulmonary activity. The pressure waveform in the right ventricle ($P_{RV}$) with both higher and lower frequencies is shown to correlate with the corresponding impedance (Imp) waveform taken from the intracardiac impedance measurements. Therefore, the intracardiac impedance measurements and the intracardiac pressure measurements within the right ventricle provide periodic and amplitude signal data from both the cardiac and the pulmonary activity of the patient.

Figure 5:
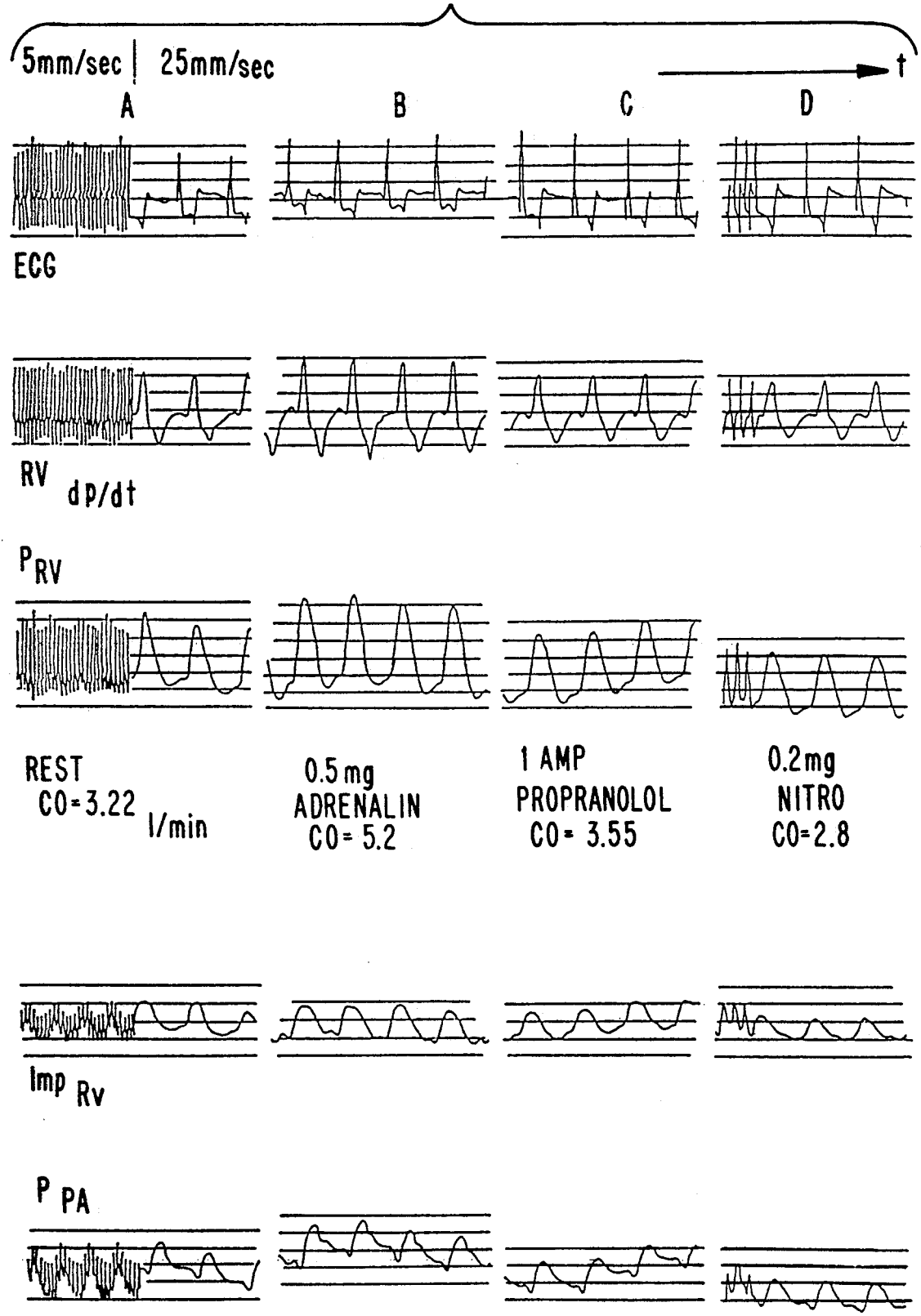

Thus, it is possible to determine the relative contractility of the heart via the systolic rate of change in time of the impedance signal during one heartbeat as seen from FIGS. 5a, b, c, d. The signal waveform RV dP/dt, representing contractility, taken from the right ventricle is thus compared with the pressure $P_{RV}$ and impedance signal Imp RV for various patient conditions, i.e., at rest and with different medications simulating different hemodynamic conditions as noted in FIG. 5 sections a, b, c and d. The various comparison waveforms show the correlation between pressure and impedance in the right ventricle and relates myocardial contractility to the rate of change of the intracardiac pressure as derived in impedance measurements as well. Note that variations in rate and amplitude are available for denoting the corresponding cardiac activity.

Figure 6:
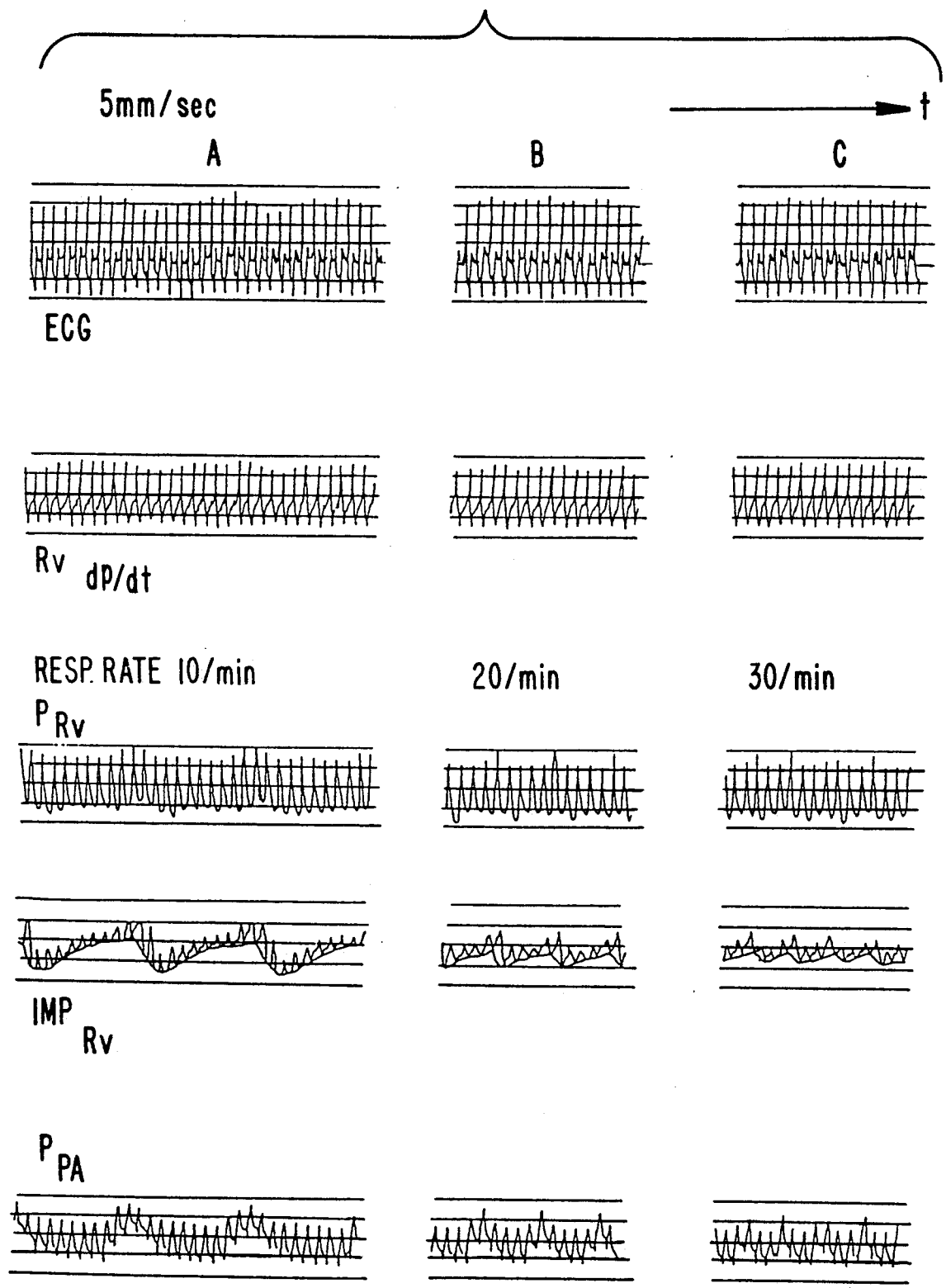

Furthermore, as evident from FIGS. 6a, b and c, not only the influence of the respiratory rate is determined from the intracardiac impedance signal, but also the depth of respiration in a dog externally ventilated. In these comparative waveform sections a, b and c, the respiratory minute volume was kept constant and the respiratory rate was increased from 10 to 20 to 30 breaths per minute. It is evident that the intracardiac impedance measurement within the right ventricle accordingly carries the periodic respiration rate information together with the depth or tidal volume information. Note that the basic parameter is a signal related to the periodic cardiac activity upon which is superimposed and modulated with signals relating to respiratory activity. Further experiments confirmed this theory in humans.

Figure 7:
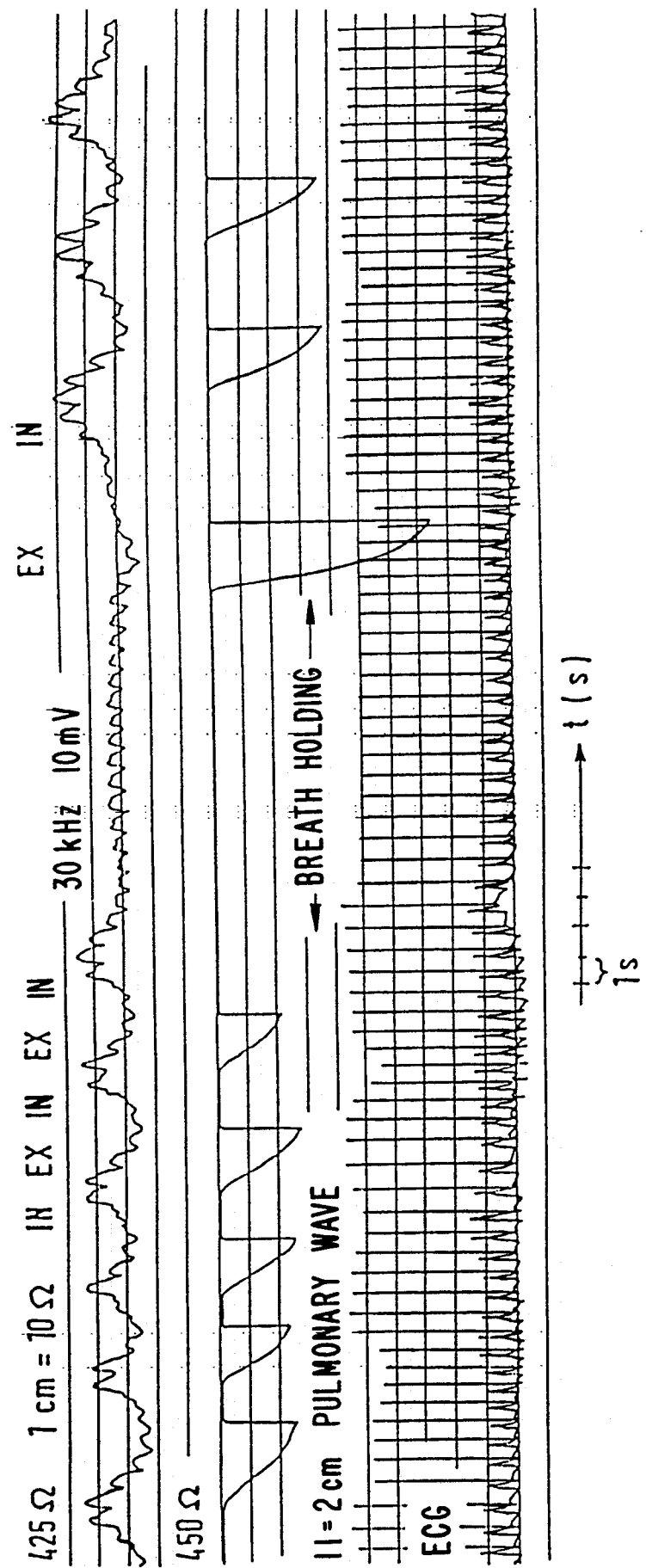
FIG. 7 shows inter-related human impedance waveforms with the lower frequency respiratory and higher frequency cardiac signal components.

As related in FIG. 7, in numerous more advanced investigations of patients and test persons we were able to prove the dependence of intracardiac impedance changes also on spontaneous breathing in humans.

FIG. 7 shows the impedance in the upper line, the directly measured exhalation (EX) in terms of time and volume in the middle line and the ECG in the lower line. The inhalation phases are clearly recognizable in the upper line by a decrease of impedance due to inhalation. The intrathoracic pressure drop during inhalation has a strong blood suction effect and thus leads to a greater filling of the right ventricle. This increase in right ventricular volume is expressed in a corresponding drop in impedance, since more blood of lower impedance is found in the vicinity of the electrode. The increase in pulmonary impedance following an increased amount of air in the lungs due to inhalation plays a negligible part in the inventive intraventricular measurement. In the phase of breath holding after inhalation it can further be seen that after initial increased filling due to inhalation the ventricle returns to its normal size again. Subsequent exhalation then leads to a further, but quite small, increase in impedance due to a further decrease of volume of the ventricle. The fine changes of impedance which correlate with the ECG are due to the right side of the heart volume changes caused by cardiac activity.

The principle of simultaneous detection of cardiac and pulmonary parameters in the heart by means of the stated principle of measurement not only opens up possibilities for rate adaptive pacemaker therapy, but also offers a good posibility of detecting and monitoring essential physiological parameters for other diagnostic or therapeutic purposes. An example is care of patients in an intensive unit, where therapeutic consequences depend on knowledge of vital data such as cardiorespiratory activity. Since many of these patients are supplied for a short time with pacemaker electrodes anyway, the data can be obtained at the same time without any additional intervention.

The preferred object of our investigations was the change in intracardiac impedance due to the influence of cardiac and respiratory activity. The use of impedance measurements is appropriate because the bipolar electrode already used routinely to stimulate the heart with both poles being located in the heart also can be used for impedance measurement. In this case no additional sensor is required.

Nevertheless, the statements made on the basis of our results also can also be applied fundamentally to the measurement of intracardiac and intravascular pressure changes with cardiac and respiratory activity. Corresponding measured data are apparent in FIGS. 5 to 7. The change of pressure behaves as a complement to volume. As a further feature of the invention, the measurement of blood flow in the heart or the surrounding vessels can also be used in the same way to determine cardiac and pulmonary changes under varying conditions, since pressure, volume and flow variations exhibit a defined dependency between each other and react predictably to pulmonary activity and to cardiac activity.

I claim:

1. Electronic medical instrumentation for determining a plurality of physiological parameters related to a patient's condition, comprising in combination:
   a single sensor adapted to be located wholly within the heart including sensor means to detect a signal varying with characteristics of the blood with corresponding signal processing means for producing from the signal detected at said sensor a variable signal including information representative of a plurality of physiological parameters of the patient related to cardiac blood flow parameters, and
   physiological activity detection means for processing the variable signal including signal processing means for separating said variable signal into subsignals respectively representative of the plurality of the patient's physiological parameters presented in said variable signal derived from blood characteristics at the in-situ position of the sensor in the heart.

2. The instrumentation of claim 1 wherein said signal processing means for separating said variable signal into subsignals further comprises separate pulmonary and cardiac activity analyzing means responsive to produce respective ones of said subsignals from said variable signal.

3. The instrumentation of claim 1 further in combination with:
   a heart pacemaker having means for generating heart pacing pulses at said single sensor, and
   control means in said pacemaker for producing heart pacing pulses responsive to changes derived as a function of said plurality of physiological parameters including parameters representative of cardiac and pulmonary activity of a patient separated as said subsignals.

4. The instrumentation of claim 3 wherein the signal processing means for producing the variable signal further comprises:
   means for generating a periodic electrical interrogation signal at said single sensor of low enough energy that the heart is not paced thereby, which interrogation signal in kind produces said variable signal in response to and varying with cardiac and pulmonary activity, and
   the signal processing means for separating the variable signal into subsignals further comprises means for producing separate said subsignals representative of pulmonary and cardiac activity of the patient.

5. The instrumentation of claim 3 wherein the corresponding means for producing the variable signal derives at the sensor means signals representative of cardiac and pulmonary activity in response to changes of pressure in the patient's cardiovascular system.

6. The instrumentation of claim 3 wherein the sensor means detects said variable signal responsive to the changes in the volume of the patient's blood in the cardiovascular system.

7. The instrumentation of claim 1 wherein the sensor means comprises a bipolar impedance detection electrode set adapted to be located in the patient's cardiovascular system.

8. The instrumentation of claim 3 wherein the sensor means detects changes in the flow of blood in the patient's cardiovascular system.

9. Electronic medical instrumentation for determining a plurality of physiological parameters related to a patient's heart activity, comprising in combination,
   detection means comprising measuring element means adapted to be located within a patient's heart with accompanying measuring means for producing a variable electrical signal containing one or more physiological parameters within the patient's heart varying with blood characteristics to include signal information responsive to both the intrathoracic pressure fluctuations acting on the heart from the patient's breathing and the internal heart activity,
   and separate signal processing channels including separation means for deriving from said variable electrical signal two subsignals respectively representative of the patient's breathing and internal heart activity for use in monitoring the patient's condition.

10. The instrumentation defined in claim 9 adapted to control heartbeat rate further comprising:
    said measuring element means comprising sensor electrode means adapted to be implanted in the right heart of the patient, a heart pacer for producing stimulation signals at said sensor electrode means, and further including heartbeat rate control means responsive to control by signals detected at said sensor electrode means from variations in blood characteristics for controlling the heartbeat rate in response to both said breathing and heart activity subsignals with impulses to said sensor electrode means, whereby the instrumentation both stimulates the heart and senses physiological activity within the heart at said sensor electrode means.

11. The instrumentation defined in claim 10 wherein said detection means further comprises impedance measuring means responsive primarily to impedance changes detechable at said sensor electrode means resulting from both pulmonary activity and cardiac activity of the patient.

12. The instrumentation defined in claim 9 wherein said separation means further comprises, filtering means for dividing the variable signal as measured wholly within the heart into said two sub-signals respectively processed by the two processing channels comprising a low frequency filter passing signals corresponding to intrathoric pressure fluctuations at the patient's breathing rate and a high frequency filter passing periodic signals of cardiac activity corresponding to the patient's cardiac activity.

13. In a cardiac heartbeat pacing system, the improvement comprising in combination, electronic heart stimulating means for inducing pacing pulses, a bipolar electrode adatpted to be implanted within the heart of a patient to receive the pacing pulses for pacing a heart, measuring means for measuring a variable wholly within the heart representative of at least one physiological factor of the patient detected at said electrode in response to periodic pulmonary activity of the patient and deriving a signal of a frequency and amplitude that represents breathing rate and tidal volume and which does not interfere with pulses at the bipolar electrode for pacing the heart of the patient, and means for modulating the signal from the pacing pulses frequency as a function of the pulmonary activity measured by the measuring means.

14. A system as defined in claim 13 wherein said measuring means includes impedance sensing means for distinguishing two said physiological factors from periodically recurring impedance changes relating to both cardiac and pulmonary activity, and band pass filter means for isolating the respective periodically recurring changes of the measured variable wholly within the heart into two differing frequency ranges by passing the respective two signals through band pass filters thereby to derive separate non-interfering signals for cardiac and pulmonary activity.

15. In a cardiac pacing method for stimulating a heartbeat with an electronic stimulation signal induced in a stimulation electrode implanted in the heart of a patient, the improvement comprising in combination the steps of, deriving a variable signal representative of a parameter exhibited wholly within the heart from said electrode with which the stimulation signal does not interfere, establishing a control signal from a restricted range of lower frequency components of said variable signal excluding higher frequency heartbeat components for the patient being monitored represenative of a physiological respiratory parameter of the patient critical to pacing, and controlling the stimulation signal as a function of the control signal.

16. The method of control of a heartbeat pacing system having a bipolar electrode implanted in a patient's heart and means for producing periodic electronic stimulation signals thereto to induce heartbeats, comprising the steps of:

measuring the impedance at a position wholly within the heart by means of the implanted bipolar electrode to produce a variable intracardiac impedance signal indicative of dynamic instantateous physiological functioning of the lungs and heart, and modulating the periodic stimulation signals with a pulmonary function derived from the variable impedance signal.

17. The method of monitoring physiological functioning of the lungs and the heart during variations of workload exercise in a patient, comprising the steps of:

developing characteristics of blood detected at an in-situ electrode within the heart in response to a variable signal having two periodic signal components respectively signifying the cardiac activity and the pulmonary activity of the patient, and separating the two periodic signal components for processing in separate channels responsive respectively to a lower frequency pulmonary activity and a higher frequency cardiac activity with said channels having a bandwith sufficient to identify modulations of rate and amplitude of the respective lower and higher frequency signal components for monitoring respectively pulmonary and cardiac activity.

18. The method of monitoring a patient's cardiac activity comprising the steps of detecting at only two separated positions within the heart of a patient a single variable impedance signal carrying separable signal components of two differing periodic frequency ranges respectively in a higher heartbeat rate range and a lower respiratory rate range, and monitoring respective signal components to obtain information pertaining to pulmonary and cardiac activity from frequency and amplitude variations of the respective two impedance signal components.

19. The method of monitoring cardiac conditions comprising the steps of determinig ventilatory parameters of a patient from an analysis of the influence of periodic intrathoracic pressure fluctuations in a signal detected by a detector electrode structure implanted wholly within the heart by a substep of isolating signal components in a restricted frequency range including the pulmonary rate and excluding the heartbeat rate with low pass filter means to derive a signal representative of said ventilatory parameters.

20. The method defined in claim 19, further providing for the step of detecting the thoracic pressure changes during ventilation of a patient comprising the substeps of implanting said detector electrode structure within the right ventricle and producing said signal that varies with the blood suction effect of pulmonary activity.

21. The method of claim 19 comprising the further steps of commonly processing in a signal processing channel a first said signal detected by said detector electrode structure representative of both instantaneous dynamic pulmonary and cardiac activity of a patient having the characteristic of insignificant reduction of the pulmonary signal component with changes in cardiac activity obtained from monitoring a single cardiac responsive parameter related to cardiac activity obtained from said electrode structure and isolating from the first said signal said pulmonary activity to produce signal components in a restricted frequency range.

22. The method of operating a stimulus electrode with bipolar electrode structure implanted wholly within the heart to control a heartbeat pulse rate comprising the steps of operating the electrode structure in a concurrent mode as a detector of intracardiac impedance of a pulmonary parameter wholly within the heart that is critical to the heartbeat pulse rate, and controlling heartbeat pulse rate by stimulus to the electrode as a function of the pulmonary parameter.

23. A heart pacemaker comprising in combination,
    pulse generator means for generating heart pacing pulses,
    a common sensor and pacing electrode adapted for location wholly within the heart and sensing means coupled thereto for deriving from parameters appearing at said sensor electrode wholly within the heart of a patient a signal modulated with a multiplicity of physiological functional parameters related to the patient's condition.
    processing means responsive to said signal to provide sub-signal components representative of said physiological parameters for respectively pulmonary activity and cardiac activity, and
    control means for changing the rate of the heart pacing pulses in response to the detected pulmonary and cardiac activity sub-signal components.

24. A heart pacemaker as defined in claim 23, wherein said common sensor and said sensing means for deriving the signal comprises:
    means for generating an electrical measurement signal of low energy unable to pace the heart to derive said signal,
    means for transmitting the measurement signal and pacing signal to the pacing electrode over a common communication channel,
    means coupled to said channel for receiving, detecting, and analizying the single signal to derive signals representative of dynamic changes in pulmonary and cardiac activity, and
    means for varying the pacing pulse rate in response to said dynamic changes.

25. A heart pacemaker as defined in claim 23 having a pacing electrode positioned in a patient's right heart, wherein said means for deriving a single signal comprises:
    pressure sensing means situated in the cardiovascular system of a patient for producing said single signal, and
    means for detecting said physiological parameters from monitoring the pressure sensed by said pressure sensing means.

26. A heart pacemaker as defined in claim 23 wherein said means for deriving a single signal comprises:
    blood flow sensing means adapted for location in a patient's cardiovascular system, and
    means for detecting said physiological parameters from monitoring blood flow sensed by said blood flow sensing means.

27. A heart pacemaker system including pulse generator means for generating heart pacing pulses, comprising in combination, blood flow sensing means adapted to be located wholly within the heart coupled with means for deriving from a patient a signal modulated with a multiplicity of physiological functional parameters relating to the patient's condition, detection means responsive to said signal to provide sub-signal components representative of said physiological parameters for cardiovascular activity, and control means for changing the rate of the pacing pulses in response to the detected cardiovascular activity sub-signal components.

* * * * *